United States Patent
Benje

(10) Patent No.: US 6,956,143 B2
(45) Date of Patent: Oct. 18, 2005

(54) PROCESS FOR DISSOLVING SALTS IN 1,2-DICHLOROETHANE USING ULTRASOUND AND A DEVICE FOR CARRYING OUT SAID PROCESS

(75) Inventor: Michael Benje, Darmstadt (DE)

(73) Assignee: Uhde GmbH, Dortmund (DE)

(*) Notice: Subject to any disclaimer, the term of this patent is extended or adjusted under 35 U.S.C. 154(b) by 118 days.

(21) Appl. No.: 10/363,599

(22) PCT Filed: Sep. 27, 2001

(86) PCT No.: PCT/EP01/11188

§ 371 (c)(1),
(2), (4) Date: Jun. 4, 2003

(87) PCT Pub. No.: WO02/30563

PCT Pub. Date: Apr. 18, 2002

(65) Prior Publication Data

US 2003/0183798 A1 Oct. 2, 2003

(30) Foreign Application Priority Data

Oct. 10, 2000 (DE) .................................. 100 50 315

(51) Int. Cl.$^7$ ............................................. C07C 17/096
(52) U.S. Cl. ........................ 570/252; 570/253; 570/262
(58) Field of Search ................................. 570/252, 253, 570/262

(56) References Cited

U.S. PATENT DOCUMENTS 3,729,543 A    4/1973   Dunn, Jr.
4,259,264 A    3/1981   Schmidhammer et al.
4,672,142 A    6/1987   Hundeck et al.

FOREIGN PATENT DOCUMENTS

| CH | 665 629 | 5/1988 |
|---|---|---|
| DE | 813 706 | 1/1953 |
| DE | 25 40 291 | 3/1977 |
| DE | 39 02 665 | 8/1990 |
| DE | 41 03 281 | 8/1992 |
| DE | 41 33 810 A | 4/1993 |
| DE | 43 18 609 A1 | 7/1994 |
| DE | 44 25 872 | 1/1996 |
| DE | 196 41 562 A1 | 1/1998 |
| EP | 0 075 742 A | 4/1983 |
| EP | 00 82 342 | 6/1983 |
| EP | 0 364 209 A | 4/1990 |
| EP | 0 775 715 A | 1/1997 |
| FR | 2 143 685 A | 2/1973 |
| FR | 2 742 352 A | 6/1997 |
| NL | 6901398 A | 11/1969 |
| WO | WO 94/17019 A1 | 8/1994 |

Primary Examiner—Johann Richter
Assistant Examiner—Sikari A. Witherspoon
(74) Attorney, Agent, or Firm—Marshall & Melhorn, LLC

(57) ABSTRACT

The invention relates to a process and a device for the dissolution of salt that is hardly soluble, especially sodium chloride and other poorly soluble salts in 1,2 dichloroethane, which primarily are to be used in direct chlorination plants for the production of 1,2 dichloroethane. This aim is achieved by mounting an ultrasonic transducer (sonotrode) in the dissolution chamber which is filled with a suspension of salt crystals and 1,2 dichloroethane. The suspension is sent through a filter upon dissolution of the salt.

6 Claims, 2 Drawing Sheets

PROCESS FOR DISSOLVING SALTS IN 1,2-DICHLOROETHANE USING ULTRASOUND AND A DEVICE FOR CARRYING OUT SAID PROCESS

BACKGROUND OF THE INVENTION

The invention relates to a process for the dissolution of salts, especially catalytically active sodium chloride NaCl and ferric chloride $FeCl_3$ in liquid 1,2 dichloroethane, hereinafter referred to as "EDC", which primarily serves as an intermediate product in the production of monomer vinyl chloride, hereinafter referred to as "VCM", which subsequently is used to produce polyvinyl chloride (PVC) by ultrasonic treatment. When EDC reacts to form VCM hydrogen chloride HCl is obtained. Hence, EDC is preferably produced from ethene $C_2H_4$ and chlorine $Cl_2$ in such a way that an equilibrated balance is maintained between the hydrogen chloride (HCl) produced and consumed in the various reactions, which is substantiated by the following reaction equations:

$$Cl_2 + C_2H_4 \rightarrow C_2H_4Cl_2(EDC) + 180 \text{ kJ/Mol} \quad (1)$$

$$C_2H_4Cl_2(EDC) \rightarrow C_2H_3Cl(VCM) + HCl - 71 \text{ kJ/Mol} \quad (2)$$

$$C_2H_4 + 2HCl + \tfrac{1}{2}O_2 \rightarrow C_2H_4Cl_2(EDC) + H_2O + 238 \text{ kJ/Mol} \quad (3)$$

Reaction (1) also referred to as direct chlorination is usually carried out as gas/liquid interfacial reaction in loop reactors of various designs, which provide for the dissolution of ethene $C_2H_4$ and thus for the speed-relevant criterion, or it takes place in the liquid phase. The EDC is applied as the solvent used for the dissolution of the reactants. Many years of practical experience have shown that the purity of the EDC produced is of major importance for the cost effectiveness and the final product purity which can be achieved by reaction (2) and consequently for the complete process. This gave way to many attempts to minimise the side reactions related to reaction (1) as, for example, by the development of efficient catalyst systems.

Reaction (1) is of the "addition type", in which generally metal halides with Lewis acid properties and a metal halide of a metal that belongs to the first main group of the periodic table are used as catalyst as well as other organic catalysts if necessary. NL-A 6901398 provides for the use of ferric chloride $FeCl_3$, sodium chloride NaCl and lithium chloride LiCl as preferred metal halides. DE 41 03 281 describes the use of a mixture of ferric chloride $FeCl_3$ and sodium chloride NaCl at a molar ratio ranging from 1 to 1.5 and 1 to 2. DE 43 18 609, in contrast to this, outlines that the reaction is especially efficient if the molar ratio of NaCl and $FeCl_3$ is kept below 0.5. In these cases, sodium chloride NaCl reacts with ferric chloride $FeCl_3$ in solution by reaction (4), thus forming sodium tetrachloroferrate $NaFeCl_4$ which has been known to be an efficient catalyst for a long time:

$$Na^+Cl^- + FeCl_3 \rightarrow Na^+FeCl_4^- \quad (4)$$

In this context, however, it is problematic that sodium chloride NaCl is hardly soluble in EDC. This also applies to the fact that under normal reaction conditions and in the presence of minor amounts of water, ferric chloride $FeCl_3$ tends to convert to hydrogen tetrachloroferrate which is known for its highly corrosive potential as described in EP 00 82 342. Such a corrosive potential can be suppressed by adding sodium chloride NaCl in a stoichiometric surplus referred to reaction with ferric chloride $FeCl_3$ according to the equation (4) so that it becomes desirable to dissolve as much sodium chloride NaCl as possible. If, however, solid sodium chloride NaCl is added to the reaction loop, solute may easily form in sections with poor flow and will not dissolve even under normal operating conditions of the direct chlorination unit and thus give way to side reactions.

As described in patent DE 25 40 291 further difficulties may also be caused by clogging as a result of inefficient solution of the sodium chloride NaCl. A specific attempt has also been described, i.e. applying instead anhydrous sodium tetrachloroferrate $NaFeCl_4$ which according to equation (4) consists of the sum of sodium chloride NaCl and ferric chloride $FeCl_3$ to be dissolved in EDC because its solubility is better than that of its components. In this case, however, the technological problem is shifted to the production of sodium tetrachloroferrate $NaFeCl_4$ which is very expensive according to U.S. Pat. No. 3,729,543.

Various attempts in the past have shown that methods to produce the preferred catalyst system are very sophisticated because the catalysts can be dissolved in the EDC reaction system with great difficulty only. DE 44 25 872 describes an example on the basis of a solution of only 170 ppm sodium chloride NaCl and 780 ppm ferric chloride $FeCl_3$.

SUMMARY OF THE INVENTION

The aim of the invention therefore is to dissolve salt, especially sodium chloride NaCl and ferric chloride $FeCl_3$, in a favourable manner and amount that preclude any disadvantage that would else occur during operation as a result of solute accumulation, in particular non-dissolved sodium chloride NaCl, and that eliminate any disadvantage coming up when a change from sodium chloride to any other, more readily soluble catalyst takes place in the direct chlorination process for EDC production; moreover that aim is to overcome any disadvantage that is normally linked to the external preparation of easily soluble catalysts.

It was a real surprise to find that the amount of sodium chloride NaCl that can be dissolved in EDC which already contains ferric chloride $FeCl_3$ in solute form is considerably larger than that hitherto achieved in production plants, provided the dissolution process is supported by ultrasonic treatment.

The process according to the invention achieves the aim defined in the previous paragraphs by providing an ultrasonic treatment of the suspension of solid, granular sodium chloride NaCl in liquid EDC which contains ferric chloride $FeCl_3$ in solute form and by providing for a subsequent filtration of said suspension.

The ultrasonic treatment generates an effect that prevents the crystal surfaces from being covered with a layer of higher molecular by-products originating from the direct chlorination reaction and being circulated in the reaction loop, that enhances the mass transfer and that precludes crystal agglomeration. This permits an efficient dissolution of the catalyst components so that no suspended solids penetrate the reaction loop.

An embodiment of the invention process provides for ferric chloride $FeCl_3$ and sodium chloride NaCl to jointly suspended in EDC. The subsequent ultrasonic treatment has the effect that ferric chloride $FeCl_3$ will dissolve first and that upon dissolution of sufficient ferric chloride, sodium chloride NaCl will dissolve in the EDC which at this stage already contains ferric chloride in solute form.

The clear solution obtained, which has a molar ratio of ferric chloride $FeCl_3$ and sodium chlorite NaCl of optionally 1:1, is admixed to the reaction fluid. The process according to the invention is suitable either for continuous operation in a side stream of the plant or for batch operation. The addition of sodium chloride NaCl to EDC and its dissolution by ultrasonic treatment may be implemented either by separate devices or by one common device.

BRIEF DESCRIPTION OF THE DRAWINGS

The details of the invention are illustrated in the attached FIGS. 1 and 2.

DESCRIPTION OF THE PREFERRED EMBODIMENTS

Figure 1:
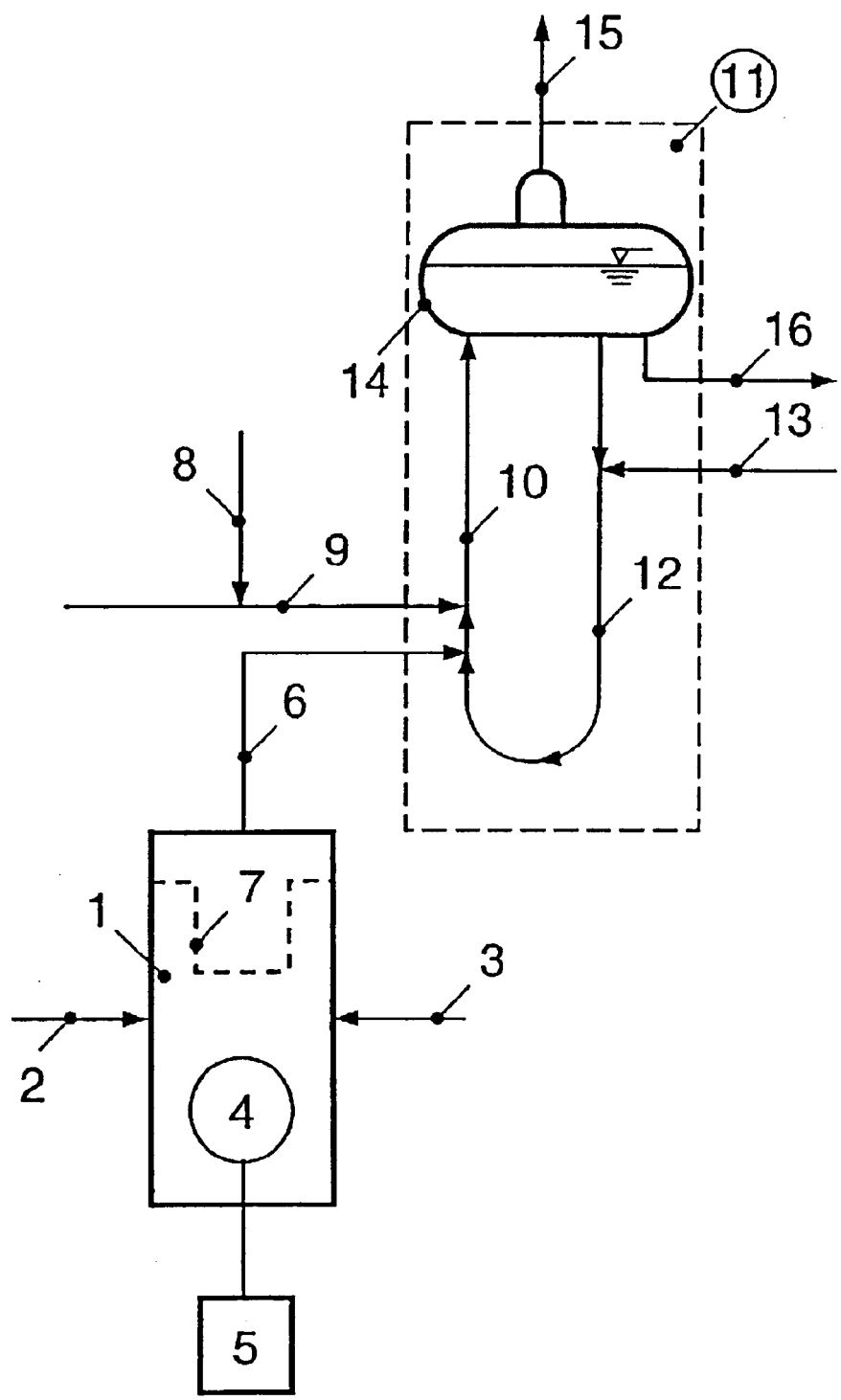
FIG. 1 schematic layout of process according to the invention

FIG. 1 shows the example of a dissolution device 1 for sodium chloride in conjunction with loop reactor 11, the sodium chloride suspension 2 being fed to dissolution device 1. As an option, sodium chloride NaCl may also be fed as bulk through an opening in or a hopper of dissolution device 1, but in this case it is essential to preclude any escape of EDC vapour because it is extremely toxic. Liquid EDC 3 is fed as solvent to dissolution device 1. Dissolution device 1 houses an ultrasonic transducer, hereinafter referred to as sonotrode 4 and connected to ultrasonic generator 5. Said sonotrode 4 emits the ultrasonic waves into the suspension. Solution 6 leaves the dissolution device 1 upon filtration in device 7.

Apart from the example of sodium chloride NaCl, it is also possible to dissolve other salts by this method, which in particular applies to metal chlorides of the first main group of the periodic system (alkaline metals) and to ferric chloride $FeCl_3$. It is also possible to dissolve salt mixtures by this method.

Said solution 6, for example, is directly injected into loop reactor 11 but without abandoning the basic idea of the invention, it is also feasible to arrange the feed point in a more favourable position in the EDC loop. Loop reactor 11 consists of chlorine dosing device 8, chlorine dissolution section 9, riser 10, downcorner 12, ethene addition facility 13 and stripper 14, the EDC produced being withdrawn either as vaporous EDC 15 or liquid EDC 16. Upon heat recovery a part stream of the EDC product stream can, for example, be re-used to dissolve sodium chloride NaCl in dissolution device 1 but without abandoning the basic idea of the invention, it is also feasible to use any other EDC part-stream of the EDC loop. The higher the temperature of that part-stream, the better it will be to carry out the dissolution according to the invention.

Figure 2:
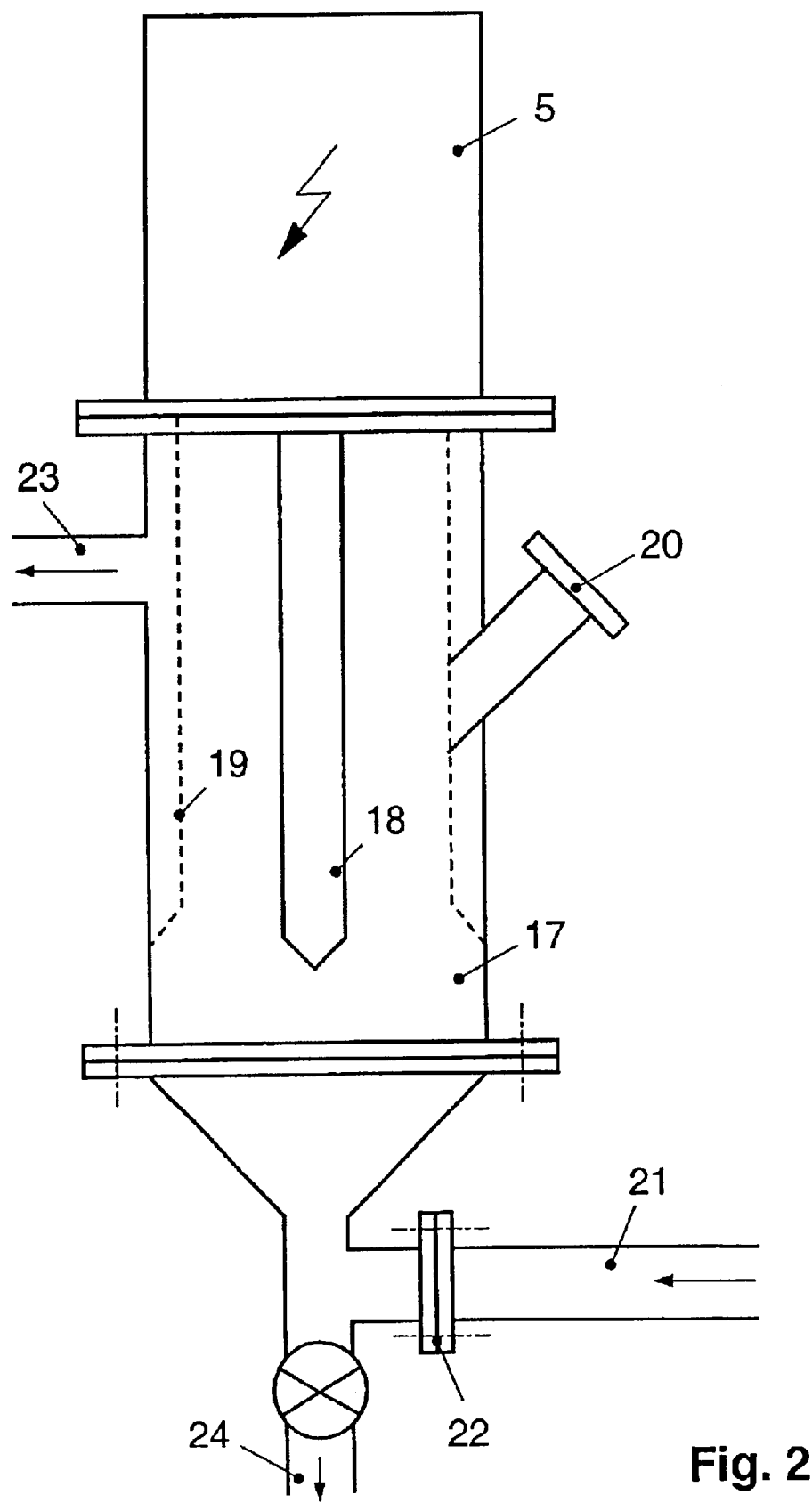
FIG. 2 schematic layout of a preferred design of the device required to implement the process

FIG. 2 shows a preferred embodiment with dissolution chamber 17, cylindrical sonotrode 18 and filtration device 19. The said assembly is suitable for batch service and for continuous operation. To feed salt to the unit it is possible to mount a feed hopper for salt (not shown in the layout) to nozzle 20. The EDC solvent is fed to dissolution chamber 17 via feed line 21 with integrated strainer 22, the solution being discharged via line 23. The suspension of the fed salt is also contained in said chamber 17 which is filled with liquid EDC at least up to the level of the discharge line and blanketed with inert gas from the gas chamber arranged above. Any salt particles contained in dissolution chamber 17 are entrained by the stream and conveyed to filtration device 19 where they are retained by the filter cake. Said filter cake and the suspension in the section surrounding the cake are subjected to ultrasonic treatment by means of the sonotrode so that the passivated layers which form on the salt crystals are continously removed and the poorly soluble salt will dissolve. It is recommended to arrange the filtration device in such a manner that a large surface area surrounds the sonotrode and that the distance from the filtration device to the sonotrode is sufficiently large to accommodate the filter cake and to preclude obstruction of the stream on the one hand, and that said distance is only a few centimetres to permit free propagation of the ultrasonic waves to the filter cake, on the other hand.

FIG. 2 also shows drain line 24 which is normally closed and ultrasonic generator 5 required to operate cylindrical sonotrode 18. The layout does not show the safety shut-off devices, the blanketing device nor the explosion-proofing equipment which the EDC specialist will of course install to meet such requirements.

What is claimed is:

1. A process for the dissolution of salts in liquid 1,2-dichloroethane, comprising providing a suspension of liquid 1,2-dichloroethane and salt particles, and subjecting said suspension to ultrasonic treatment.

2. A process according to claim 1, wherein the salt particles were dissolved in the ultrasonic treatment and the dissolved salt was used as a catalyst for the production of 1,2-dichloroethane in a direct chlorination plant.

3. A process according to claim 1, wherein the suspension subsequent to said ultrasonic treatment is filtered.

4. A process according to claim 1, wherein said salt particles include at least in part an alkali chloride.

5. A process according to claim 4, wherein said alkali chloride is sodium chloride.

6. A process according to claim 1, wherein said salt particles include at least in part a ferric chloride.

* * * * *